United States Patent [19]
Yoshimura et al.

[11] Patent Number: 4,746,743
[45] Date of Patent: May 24, 1988

[54] PROCESS FOR PRODUCING 2,2,4-TRIMETHYL-1,2-DIHYDROQUINOLINE

[75] Inventors: Masakatsu Yoshimura, Sakai; Takeo Fujii, Toyonaka; Kikumitsu Inoue, Nishinomiya; Masahito Umehara, Toyonaka; Hideo Nagasaki, Osaka, all of Japan

[73] Assignee: Sumitomo Chemical Company, Limited, Osaka, Japan

[21] Appl. No.: 747,554

[22] Filed: Jun. 21, 1985

[30] Foreign Application Priority Data

Jun. 29, 1984 [JP] Japan .................. 59-135995

[51] Int. Cl.$^4$ .......................... C07D 215/06
[52] U.S. Cl. .................................. 546/181
[58] Field of Search ......................... 546/181

[56] References Cited

U.S. PATENT DOCUMENTS 2,514,648 7/1950 Kehe .................. 546/181
3,020,282 2/1962 Cislak et al. ........... 546/181

FOREIGN PATENT DOCUMENTS 1932022 1/1971 Fed. Rep. of Germany ...... 546/181
57-11967 1/1982 Japan .
0088363 5/1983 Japan ........................ 546/161

OTHER PUBLICATIONS

Olah, "Friedel Crafts and Related Reactions", Interscience, N.Y., N.Y., pp. 230 and 325, 1963.
Tarnowski et al., C.A., 98, (1983) Abst. #89192h.

Primary Examiner—Glennon H. Hollrah
Assistant Examiner—D. B. Springer
Attorney, Agent, or Firm—Wenderoth, Lind & Ponack

[57] ABSTRACT

Process for producing 2,2,4-trimethyl-1,2-dihydroquinoline by reacting aniline with an acetone compound at 80°–150° C. in the presence of, as catalyst, both hydrogen fluoride and boron trifluoride.

2 Claims, No Drawings

PROCESS FOR PRODUCING 2,2,4-TRIMETHYL-1,2-DIHYDROQUINOLINE

This invention relates to a process for producing 2,2,4-trimethyl-1,2-dihydroquinoline.

2,2,4-Trimethyl-1,2-dihydroquinoline is a useful antioxidant for polymers and also is of use as a synthetic intermediate for various antioxidants for polymers. It is known that this compound can be prepared by condensation of aniline with acetone, diacetone alcohol or mesityl oxide (these and mixtures thereof are hereinafter collectively called "acetone derivative") at elevated temperatures in the presence of an acid catalyst such as hydrochloric acid and iodine. It is also known that reaction using such an acid catalyst gives, besides monomeric 2,2,4-trimethyl-1,2-dihydroquinoline (hereinafter referred to simply as "monomer"), its polymers (hereinafter referred to simply as "polymer") and many other impurities: Rubber Chemistry & Technology, 53, 346–356 (1980).

For example, methods have been disclosed in which acetone is allowed to act at 100° C. over a period of 5.5 hours upon aniline containing 0.03 molar proportion of hydrochloric acid as catalyst, and in which acetone is allowed to act at 130° to 140° C. over a period of six hours upon aniline containing 1/7.5 molar proportion of hydrochloric acid as catalyst. In the former case, only about 28% of monomer and about 13% of residue were obtained, with the major portion of aniline being left unreacted. In the latter case, the monomer was obtained only in about 19% yield, leaving about 64% of the polymer and other residue.

Use of p-toluenesulfonic acid, benzenesulfonic acid and other acids as catalysts has also been proposed. The yield of the monomer is not higher than about 60% in this case too.

In order to achieve higher yield of 2,2,4-trimethyl-1,2-dihydroquinoline, the present inventors formerly proposed a method in which boron trifluoride/aniline complex is employed as catalyst: Japanese Patent Application Laid-open No. 11967 (1982). Even with this method, the yield of monomer is still about 69%—a level far from satisfactory.

Further studies have led us to find that the yield of monomer can be markedly enhanced if a combination of boron trifluoride and hydrogen fluoride, in place of boron trifluoride alone, is used as catalyst. This invention was accomplished based on this finding.

Thus this invention provides an improved method for producing 2,2,4-trimethyl-1,2-dihydroquinoline by reaction of aniline with an acetone derivative, wherein a catalyst composed of hydrogen fluoride and boron trifluoride is employed to achieve higher yield of the monomer.

The catalyst used in this invention is a mixture of hydrogen fluoride (HF) and boron trifluoride ($BF_3$) normally at a molar ratio from 1:5 to 2:1. Commercially available fluoboric acid (in which $HF:BF_3$ molar ratio is 1:1) may also be advantageously employed.

The suitable amount of catalyst (sum of hydrogen fluoride and boron trifluoride) is in the range from 0.005 to 0.1 mole per mole of aniline, but an amount in the range from 0.01 to 0.07 mole is preferable in terms of reaction rate and economy. The two components may be premixed prior to addition to aniline, or may be mixed with aniline separately.

There is no specific limitation upon the other reaction conditions (the reaction may be conducted under any known conditions). However, it is preferable that an acetone derivative (in an excess amount) be continuously fed to the reaction system at a temperature in the range from 80 to 150° C. over a period of 2 to 16 hours, with the unreacted portion being continuously distilled off and recovered in the form of acetone. This aids in retarding side reactions and allows the reaction to proceed under normal pressure at a constant temperature.

The following Examples further illustrate this invention but are not intended to limit its scope.

EXAMPLE 1

Aniline (420 g, 4.51 moles), 45% hydrofluoric acid (6.23 g, 0.14 mole) and boron trifluoride hydrate (13.3 g; $BF_3$ content: 71.5%, 0.14 mole) were placed in a one-liter, four-necked flask fitted with an inlet for acetone derivative, a distillation column with a dephlegmator, a thermometer and a stirrer, the mixture was heated to 120° C., and acetone (1310 g, 22.6 moles) was added over a period of 10 hours while maintaining the internal temperature at 120° to 125° C. During this time, unreacted acetone and other low-boiling compounds were led to the distillation column, and acetone was recovered from its top. Aniline and water were collected from the bottom, of which aniline was recycled back to the flask. A clear, yellowish-red liquid was left at the end of reaction, but no solid was detected at all.

The internal temperature was increased to 140° to 145° C., the flask was gradually evacuated, and unreacted aniline (30.3 g) was collected at 20 Torr. When the temperature was further raised to 160° C., the monomer began to distil off at 15 Torr, giving 577.5 g of monomer (purity: 95%) by decreasing the pressure to 3 Torr. Distillation was continued while raising the internal temperature to 190° C., affording 102.7 g of the monomer (purity: 92%). The total yield was 643.1 g, 82.3% based on the aniline charged.

EXAMPLE 2

Aniline (420 g, 4.51 moles), 45% hydrofluoric acid (8.02 g, 0.18 mole) and boron trifluoride hydrate (8.55 g, 0.09 mole) were placed in a flask of the same type as used in Example 1, the mixture was heated to 140° C., and mesityl oxide (531.1 g, 5.41 moles) was added over a period of four hours while maintaining the internal temperature at 140° to 145° C. In this case, too rapid addition of mesityl oxide tends to lower the reaction temperature and leads to lower rate of conversion because hydrolysis of unreacted mesityl oxide proceeds to form acetone in a large quantity; hence, great care was taken to add it evenly over the period of four hours. The water released by the reaction was distilled off under normal or slightly reduced pressure.

After all the mesityl oxide was added, the temperature was maintained at 140° to 150° C. for about one hour, followed by recovery of aniline and distillation of the monomer in the same way as Example 1.

The amount of aniline recovered was 20.5 g. The yield of monomer was 605.9 g for 96.5%-purity product (fraction up to 160° C./3 Torr) and 68.4 g for 91.4%-purity product (fraction up 190° C./3 Torr). The total yield was 82.8% based on the amount of aniline charged.

EXAMPLES 3 through 8

Reactions similar reaction to Examples 1 and 2 were carried out under the conditions shown in Table 1.

TABLE 1

| Ex. | HF/BF$_3$ (mole ratio) | HF + BF$_3$/ Aniline (mole ratio) | Acetone Derivative | Reaction Temp./ Time (°C./Hr) | Yld. of Monomer (%) |
|---|---|---|---|---|---|
| 3 | 1* | 0.025 | Acetone | 150/6 | 82.1 |
| 4 | 1* | 0.05 | Diacetone alcohol | 80/12 | 85.0 |
| 5 | 0.2 | 0.07 | Diacetone alcohol | 80/16 | 81.2 |
| 6 | 1.5 | 0.03 | Mesityl oxide | 130/5 | 84.4 |
| 7 | 0.5 | 0.03 | Acetone | 120/6 | 80.0 |
| 8 | 1* | 0.025 | Mesityl oxide | 120/8 | 83.6 |

*Commercial fluoboric acid used.

COMPARATIVE EXAMPLE 1

Acetone (523 g) was added to a mixture of aniline (139.7 g, 1.5 moles) and p-toluenesulfonic acid monohydrate (14.3 g) over a period of six hours while maintaining the temperature at 140° to 145° C. Treatment in the same way as in Example 1 gave 165.7 g of monomer (93.3% purity) and 61.8 g of residue (containing 12.9 g p-toluenesulfonic acid).

The yields of monomer and residue based on the amount of aniline charged were 59.5% and 18.8%, respectively.

COMPARATIVE EXAMPLE 2

In a similar way to Example 1, one liter of acetone was introduced into a mixture of aniline (93 g, 1.0 mole) and benzenesulfonic acid (2 g, 0.013 mole) over a period of eight hours while maintaining the temperature at 150° to 160° C. The reaction mixture was held at that temperature for an additional 30 minutes. Vacuum distillation gave 69.7 g (0.383 mole) of monomer (95.2% purity). The yield based on aniline was 38.3%.

COMPARATIVE EXAMPLE 3

Acetone (871.2 g) was introduced into a mixture of aniline (139.7 g, 1.5 moles) and BF$_3$/aniline complex (8.3 g) over a period of eight hours while maintaining the temperature at 100° to 105° C. Treatment in the same was as in Example 1 gave 191.1 g of monomer (94.1% purity) and 40.4 g of residue (containing 3.5 g BF$_3$). Insoluble solid substances were found in the residue and on the wall of the flask.

The yields of monomer and residue based on the amount of aniline charged were 69.2% and 14.2%, respectively.

What we claim is:

1. In a process for producing 2,2,4-trimethyl-1,2-dihydroquinoline by reacting aniline with at least one member selected from the group consisting of acetone, diacetone alcohol and mesityl oxide at a temperature of 80°–150° C. in the presence of a catalyst, the improvement which comprises using, as said catalyst, a catalyst consisting essentially of hydrogen fluoride and boron trifluoride, the molar ratio of hydrogen fluoride/boron trifluoride being 0.2–2/1 and the total amount of the hydrogen fluoride and boron trifluoride being 0.005 to 0.1 mole per mole of aniline.

2. A process according to claim 1 wherein the total amount of the hydrogen fluoride and boron trifluoride is 0.01 to 0.07 mole per mole of the aniline.

* * * * *